United States Patent
Greiner et al.

(10) Patent No.: US 6,667,099 B1
(45) Date of Patent: Dec. 23, 2003

(54) MESO- AND NANOTUBES

(75) Inventors: Andreas Greiner, Amöneburg (DE); Joachim Wendorff, Marburg (DE); Johannes Averdung, Gelsenkirchen (DE); Michael Dröscher, Dorsten (DE)

(73) Assignee: Creavis Gesellschaft fuer Technologie und Innovation mbH, Marl (DE)

(*) Notice: Subject to any disclaimer, the term of this patent is extended or adjusted under 35 U.S.C. 154(b) by 0 days.

(21) Appl. No.: 10/048,163

(22) PCT Filed: Jul. 13, 2000

(86) PCT No.: PCT/EP00/06671
§ 371 (c)(1),
(2), (4) Date: Jan. 29, 2002

(87) PCT Pub. No.: WO01/09414
PCT Pub. Date: Feb. 8, 2001

(30) Foreign Application Priority Data

Jul. 29, 1999 (DE) .......................... 199 35 388

(51) Int. Cl.⁷ ................................ D01F 6/00
(52) U.S. Cl. .................. 428/398; 428/364; 428/397; 428/376; 264/29.1
(58) Field of Search .................. 428/376, 397, 428/364, 34.4, 398

(56) References Cited

U.S. PATENT DOCUMENTS

| | | | |
|---|---|---|---|
| 5,094,906 A | | 3/1992 | Witzke et al. |
| 5,298,298 A | * | 3/1994 | Hoffman ............... 428/34.4 |
| 5,352,512 A | * | 10/1994 | Hoffman ............... 428/311.5 |
| 6,194,066 B1 | * | 2/2001 | Hoffman ............... 428/367 |

FOREIGN PATENT DOCUMENTS

| | | |
|---|---|---|
| DE | 28 23 521 | 12/1979 |
| EP | 0 195 353 | 9/1986 |
| FR | 1 511 581 | 4/1968 |
| JP | 62 110916 | 5/1987 |
| WO | 97 26225 | 7/1997 |
| WO | 99 18893 | 4/1999 |

* cited by examiner

*Primary Examiner*—N. Edwards
(74) *Attorney, Agent, or Firm*—Oblon, Spivak, McClelland, Maier & Neustadt, P.C.

(57) ABSTRACT

The invention relates to mesotubes and nanotubes (hollow fibers) having an inner diameter of 10 nm–50 μm and to a method for the production thereof. The hollow fibers can be produced by coating degradable materials with non-degradable materials, whereby the degradable materials are destroyed by thermal methods, for instance. The hollow fibers are used in separation technology, catalysis, microelectronics, medical technology, material technology or in the clothing industry.

47 Claims, 12 Drawing Sheets

MESO-AND NANOTUBES

Figure 1:
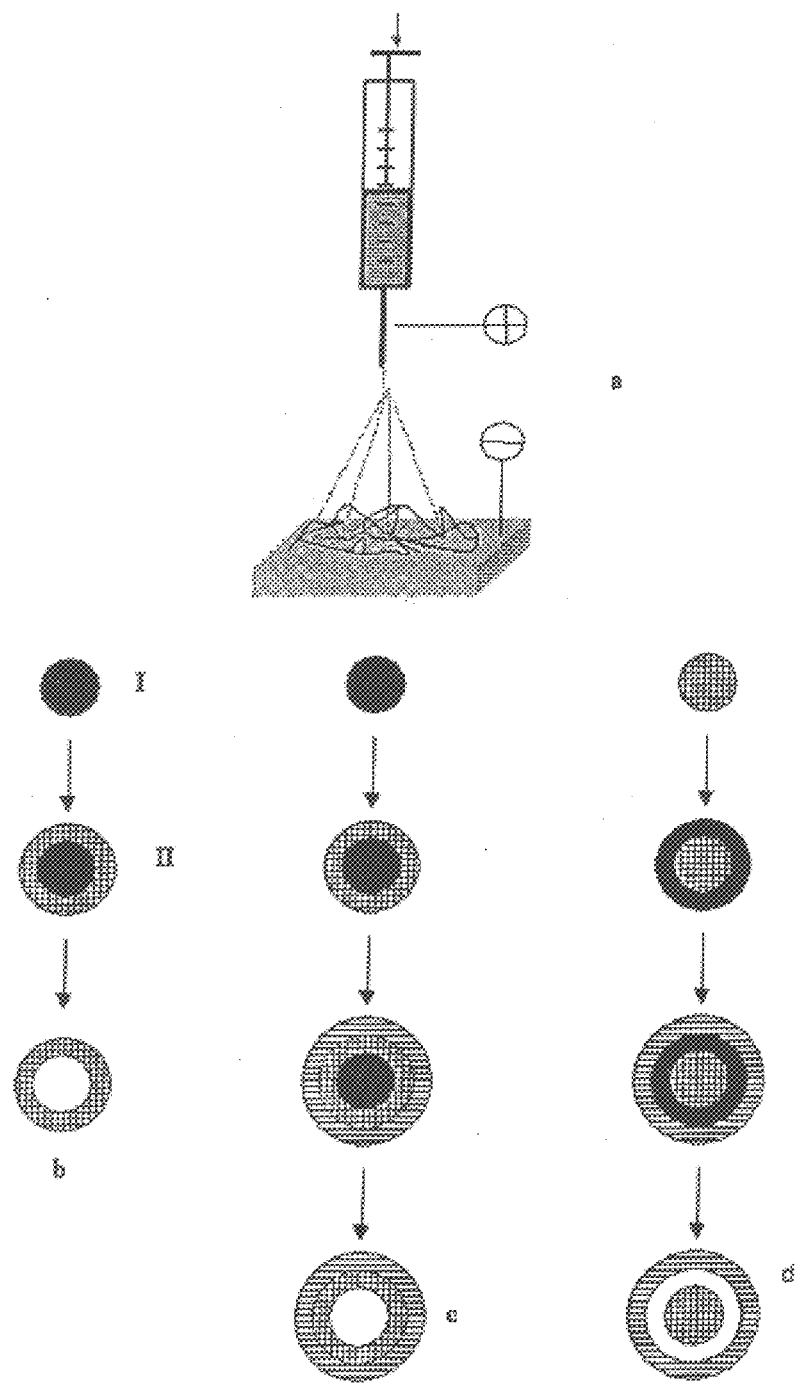

The invention relates to meso- and nanotubes, i.e. tubes or hollow fibers having an internal diameter in the nanometer to micron region, to a process for their production, and to the use of these tubes or hollow fibers.

The term hollow fibers, mesotubes or nanotubes is taken to mean tubes having an internal diameter of less than 0.1 mm.

Tubes or hollow fibers having small internal diameters are known and are employed, in particular, for separation purposes, for example in medical dialysis, for gas separation or osmosis of aqueous systems, for example for water treatment (see Kirk-Othmer, Encyclopedia of Chemical Technology, $4^{th}$ Ed., Vol. 13, pp. 312–313). The fiber material usually consists of polymers, which may in addition have pores, i.e. properties of semi-permeable membranes. The hollow fibers used for separation purposes usually have a surface area of 100 cm$^2$ per cm$^3$ of volume with an internal diameter of from 75 $\mu$m to 1 mm.

A further application of hollow fibers is in microelectronics. Here, supraconducting fibers about 60 $\mu$m in diameter are produced from supraconducting material by filling hollow fibers made from polymers with a material which, after thermal degradation of the polymer, has supraconducting properties (J. C. W. Cien, H. Rinsdorf et al., Adv. Mater., 2 (1990) p. 305).

Tubes of small internal diameter are generally produced by extrusion spinning processes; a number of extrusion spinning processes are described in Kirk-Othmer, Encyclopedia of Chemical Technology, $4^{th}$ Ed., Vol. 13, pp. 317–322.

With the aid of extrusion spinning processes, hollow fibers having an internal diameter of up to 2 $\mu$m can be produced. The production of hollow fibers having smaller internal diameters is not possible by this process. Very thin fibers without a cavity can be produced using the electrostatic spinning method. Here, polymer melts or polymer solutions are extruded through cannulas under a low pressure in an electric field. The principles of this method are given, for example, in EP 0 005 035, EP 0 095 940, U.S. Pat. No. 5,024,789 or WO 91/01695. With the aid of the electrostatic spinning method, solid fibers having a diameter of 10–3000 nm can be produced; however, the production of hollow fibers is not possible by this method either.

Hollow fibers having a very small internal diameter have hitherto only been accessible by electrochemical synthesis, as described in L. A. Chemozantonskii, Chem. Phys. Lett. 297, 257, (1998), by the methods of supramolecular chemistry (S. Demoustier-Champagne et al., Europ. Polym. J. 34, 1767, (1998), or using self-organizing membranes as templates (E. Evans et al., Science, Vol. 273, 1996, pp. 933–995). Hollow carbon fibers based on fullerene chemistry (carbon nanotubes having single- or multi-wall structures made from a single rolled-up graphite layer (layer of six-membered carbon rings fused to one another on all sides) or concentrically arranged graphite cylinders are described, for example, in "Fullerenes and related structures", Ed. A. Hirsch, Springer Verlag 1999, pp. 189–234, or N. Grobert, Nachr. Chem. Tech. Lab., 47 (1999), 768–776.

Hollow fibers of ceramic materials are described in WO 97/26225, EP 0 195 353 and U.S. Pat. No. 5,094,906, hollow fibers of metals having an internal diameter of from 1 to 1000 $\mu$m are described in FR 1 511 581 and DE28 23 521.

However, these methods can only be applied to specific materials and cannot be employed for the production of industrially useful, i.e. mechanically and chemically stable, hollow fibers.

It would be desired for many applications, for example in the separation of gases, to employ hollow fibers having small external and/or internal diameters made from various materials matched to the respective area of application. In particular, the materials should be capable of withstanding thermal, mechanical and chemical loads, if desired have a porous structure, should be either electrical conductors or insulators and should consist of polymers, inorganic materials or metals.

The object of the present invention was therefore to provide hollow fibers of industrially usable materials having an internal diameter in the nm to $\mu$m range.

Surprisingly, it has been found that hollow fibers having an internal diameter in the desired dimensions can be produced precisely and from an extremely wide variety of materials, such as polymers, inorganic materials or even metals.

The present invention relates to hollow fibers having an internal diameter of from 10 nm to 1 $\mu$m and an outer wall built up from metals and/or polymers.

The hollow fibers according to the invention preferably have internal diameters of from 100 nm to 1 $\mu$m, from 500 nm to 1 $\mu$m, from 10 nm to 1 $\mu$m or from 100 nm to 500 nm.

The length of the hollow fibers is determined by the application and is generally from 50 $\mu$m to several mm or cm.

The wall thickness, i.e. the thickness of the outer walls of the hollow fibers, is variable and is generally from 10 to 5000 nm, preferably from 10 to 1000 nm, particularly preferably from 10 to 250 nm.

Besides the very small internal diameters, hollow fibers in accordance with the present invention have a number of properties which make them suitable for use in the areas of medicine, electronics, catalysis, chemical analysis, gas separation, osmosis or optics.

Thus, the outer walls of the hollow fibers according to the invention can be built up from an extremely wide variety of materials, such as, for example, from polymers, metals or inorganic metal-containing compounds. The outer walls can have one layer of these materials, i.e. can consist entirely thereof, or have a plurality of layers made from identical or different materials. The very small internal diameter ensures a very high ratio between surface area and volume of the hollow fibers; this can be between 500 and 2,000,000 cm$^2$/cm$^3$, preferably from 5000 to 1,000,000 cm$^2$/cm$^3$, particularly preferably from 5000 to 500,000 cm$^2$/cm$^3$.

For the purposes of the present invention, polymers are polycondensates, polyaddition compounds or products of chain growth polymerization reactions, but not graphite-like compounds of pure or doped carbon.

The present invention furthermore relates to a process for the production of the hollow fibers.

The process for the production of the hollow fibers according to the invention can be carried out by coating, at least once, a fiber of a first, degradable material with polymers and/or metals and subsequently degrading the first material, with the proviso that the hollow fiber obtained in this way has an internal diameter of from 10 nm to 1 $\mu$m.

The hollow fibers according to the invention can also contain a core, for example as shown in FIG. 1$d$. In another embodiment of the present invention, a first, non-degradable material is coated successively with a second, degradable material and at least one further material, and the second, degradable material is degraded, with the proviso that, based on the at least one further material, a hollow fiber having an internal diameter of from 10 nm to 1 $\mu$m, an outer wall of polymers and/or metals and a core of the first material is obtained.

In the case of hollow fibers according to the invention having a core, the latter preferably has a mean distance from the outer wall of from 10 to 300 nm and can be built up from carbon fibers, ceramic fibers, polymers and/or metals. Preferred materials are presented below.

FIGS. 1b), c) and d) show possible embodiments of the hollow fibers and of the process for their production.

In one variant, a fiber (FIG. 1b, I) of a first, degradable material is firstly coated (FIG. 1b, II). This fiber can consist of a thermally, chemically, radiochemically, physically, biologically, plasma-, ultrasound- or solvent extraction-degradable material. These fibers can be produced using the electrostatic spinning method.

Details on the electrostatic spinning method are given, for example, in D. H. Reneker, I. Chun, Nanotechn. 7, 216 (1996). The principle of the construction of an electrostatic spinning apparatus is shown in FIG. 1a.

The diameter of the degradable fibers should be in the same order of magnitude as the later desired internal diameter of the hollow fibers. In general, the later cavity of the hollow fibers is of approximately the same size as the diameter of the degradable fibers or coatings. The precise dimensions depend on the materials used and their changes during the degradation process and can be determined without difficulty by preliminary experiments.

Degradable fiber materials which can be employed are organic or inorganic materials, in particular polymers, such as polyesters, polyethers, polyolefins, polycarbonates, polyurethanes, natural polymers, polylactides, polyglycosides, poly-α-methylstyrene and/or polyacrylonitriles. The electrostatic spinning method furthermore allows the production of multi-component fibers, i.e. fibers containing different materials in different layers or fibers having a certain surface topography, i.e. having smooth or porous surfaces.

The surface nature of the fibers or layer of the degradable material also determines the surface topography of the subsequent coatings. If, for example, a rough or microstructured inside of the hollow fibers is desired, this can be achieved by means of a correspondingly rough fiber of a degradable material. Rough or microstructured fibers can be obtained by the electrostatic spinning method by processing of a polymer solution containing a volatile solvent. Furthermore, additives, such as salts, for example sodium sulfate, metallic nanopowders, conductive polymers, such as polypyrroles, or graphite, can significantly increase the conductivity of the spun material.

The coating with the at least one further non-degradable material can be carried out by gas-phase deposition, plasma polymerization or by application of the material in a melt or in solution. The coating can be carried out in various layers and with various materials and forms the outer wall of the hollow fibers.

This coating, i.e. the build-up of the outer wall, can be carried out, for example, by gas-phase deposition, knife coating, spin coating, dip coating, spraying or plasma deposition of polymers, such as poly(p-xylylene), polyacrylamide, polyimides, polyesters, polyolefins, polycarbonates, polyamides, polyethers, polyphenylene, polysilanes, polysiloxanes, polybenzimidazoles, polybenzothiazoles, polyoxazoles, polysulfides, polyester amides, polyarylenevinylenes, polylactides, polyether ketones, polyurethanes, poly-sulfones, ormocers, polyacrylates, silicones, fully aromatic copolyesters, poly-N-vinylpyrrolidone, polyhydroxyethyl methacrylate, poly-methyl methacrylate, polyethylene terephthalate, polybutylene terephthalate, polymethacrylonitrile, polyacrylonitrile, polyvinyl acetate, neoprene, Buna N, polybutadiene, polytetrafluoroethene, cellulose (modified or unmodified), alginates or collagen, homopolymers or copolymers and/or blends thereof.

The degradable layers or fibers may furthermore be coated with a further material obtained by polymerization of one or more monomers. Suitable monomers for the homo- or copolymerization are, for example, methacrylate, styrene, styrene sulfonate, 1,6-hexamethylene diisocyanate (HDI), 4,4'-methylenebiscyclohexyl diisocyanate (HMDI), 4,4'-methylenebis(benzyl diisocyanate) (MDI), 1,4-butanediol, ethylenediamine, ethylene, styrene, butadiene, 1-butene, 2-butene, vinyl alcohol, acrylonitrile, methyl methacrylate, vinyl chloride, fluorinated ethylenes or terephthalates.

The coating, i.e. the build-up of the outer wall of the hollow fibers, can consist of metals from groups Ia, Ib, IIa, IIb, IIIa, IIIb, IVa, IVb, Vb, VIb, VIIb and/or VIIIb of the Periodic Table, in each case as the pure metal or an alloy. Suitable metals are, for example, gold, palladium, aluminum, platinum, silver, titanium, cobalt, ruthenium, rhodium, sodium, potassium, calcium, lithium, vanadium, nickel, tungsten, chromium, manganese and/or silicon. The coating can be carried out by vapor deposition with the metals or by decomposition of suitable organometallic compounds using CVD methods.

Polymeric coating materials may furthermore carry functional groups, such as esters, amides, amines, silyl groups, siloxane groups, thiols, hydroxyl groups, urethane groups, carbamate groups, nitrile groups, C=C groups, C≡C groups, carboxylic acid halide groups, sulfoxide groups, sulfone groups, pyridyl groups, arylphosphine groups or alternatively ionic groups, such as carboxylic acids, sulfonic acids or quaternary amines. The functional groups can be applied to the inside and/or outside of the hollow fibers and may improve the surface properties of the hollow fibers in separation or osmosis processes. The functional groups can also subsequently be chemically modified by polymer-analogous reactions (for example hydrolysis of esters).

Through an appropriate functionalization, it is also possible for active ingredients, such as antibiotics, anesthetics, proteins, such as insulin, antifouling agents and agrochemicals, such as herbicides or fungicides, to be fixed reversibly in the hollow fibers and/or released again slowly with constant concentration (controlled or slow release).

The degradation of the degradable material can be carried out thermally, chemically, radiation-induced, biologically, photochemically, by means of plasma, ultrasound, hydrolysis or by extraction with a solvent. In practice, thermal degradation has proven successful. The decomposition conditions are, depending on the material, 100–500° C. and from 0.001 mbar to 1 bar, particularly preferably from 0.001 to 0.1 mbar. Degradation of the material gives a hollow fiber whose wall material consists of the coating materials.

As shown in FIGS. 1b, c and d, it is also possible for a plurality of layers of different materials to be applied to the fibers. In this way, hollow fibers are obtained which have different inner and outer walls, or the outer walls of the hollow fibers can be built up from a plurality of layers. The different layers can fulfill different functions; thus, the inner layer can have particular separation properties for, for example, chromatographic purposes and the outer layer can have high mechanical stability.

The following layer sequences of the hollow fibers according to the invention may be mentioned by way of example:
glass/metal
metal/glass
glass/polymer
polymer/glass
polymer/polymer
metal/metal
inorganic metal-containing compound/inorganic metal-containing compound
ceramic/ceramic
polymer/metal
metal/polymer
ceramic/polymer
polymer/ceramic
metal/ceramic
ceramic/metal
polymer/metal/polymer
metal/polymer/metal
metal/ceramic/metal
polymer/ceramic/polymer
ceramic/polymer/ceramic
polymer/glass/polymer
glass/polymer/glass Hollow fibers according to the invention with or without a core can be used, in particular, as separation or storage medium for gases, liquids or particle suspensions and for the filtration or purification of substance mixtures. Possible uses here are as membranes for gases, in particular $H_2$ or liquids, for particle filtration, in chromatography, for oil/water separation, as ion exchangers in dialysis, for size separation of cells, bacteria or viruses, as a constituent of an artificial lung, for desalination for water removal or irrigation or as a filter for dewatering of fuels.

Hollow fibers according to the invention may furthermore be used in sensor technology for solvent, gas, moisture or biosensors, in capillary electrophoresis, in catalytic systems, in scanning probe microscopy or as materials in superlight construction, as mechanical reinforcement analogously to glass fibers, as sound or vibration protection as a composite material or filler, as a controlled release or drug delivery system, in medical separation methods, in dialysis, as an artificial lung, protein store or in tissue engineering.

In the clothing/textiles industry, the hollow fibers according to the invention can be used as thermal insulator in clothing or sleeping bags, in photochromic or thermochromic clothing through embedding of dyes in the interior of the tubes or as labels through markers in the interior of the tubes.

Hollow fibers according to the invention are also used in electronics, optics or energy recovery. For example, the hollow fibers can be used for the production of wires, cables or capacitors, micromachines (for example for piezoelectric shaping, nanoperistaltic pumps or for the shaping of photo-addressable polymers) or interlayer dielectrics. Further uses of hollow fibers according to the invention are microreactors, for example for catalytic reactors, template reactions and bioreactors, heat generation through conversion of sunlight (solar α systems), in chip technology as flexible devices or microscopy as a sensor constituent (for example as tips or probes for scanning probe microscopes or SNOM instruments).

The hollow fibers according to the invention have a very low dielectric constant and can therefore also be used as a dielectric, in particular as an interlayer dielectric in electronic components, for example in chip manufacture. In the production of new chip generations with even smaller dimensions or higher storage densities, interlayer dielectrics having a low dielectric constant are important. Owing to the high proportion of included air per volume unit, the hollow fibers according to the invention have a dielectric constant of less than 4, preferably less than 3, very particularly less than 2 and in the ideal case less than 1.5.

Figure 2:
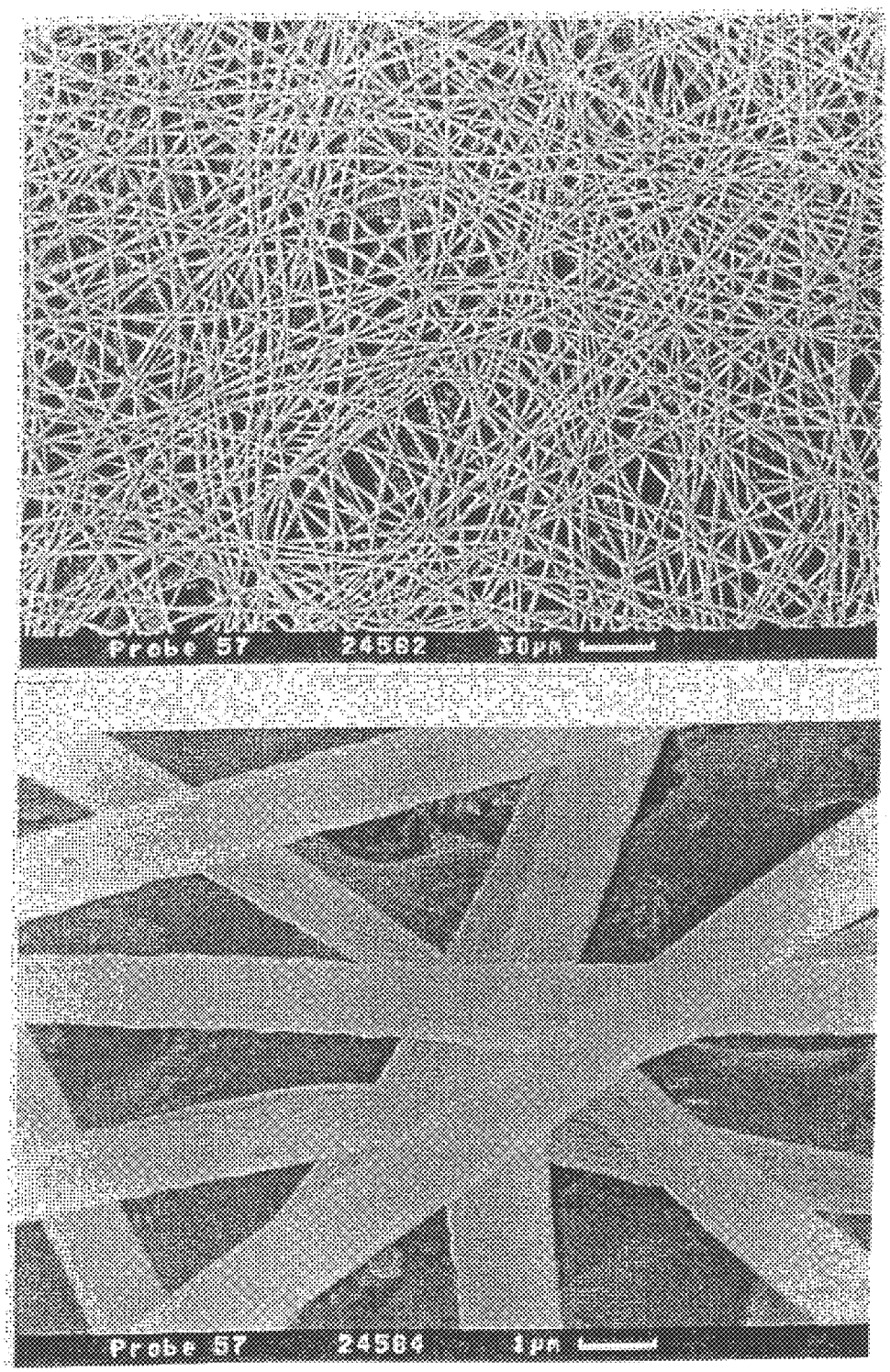
Figure 3:
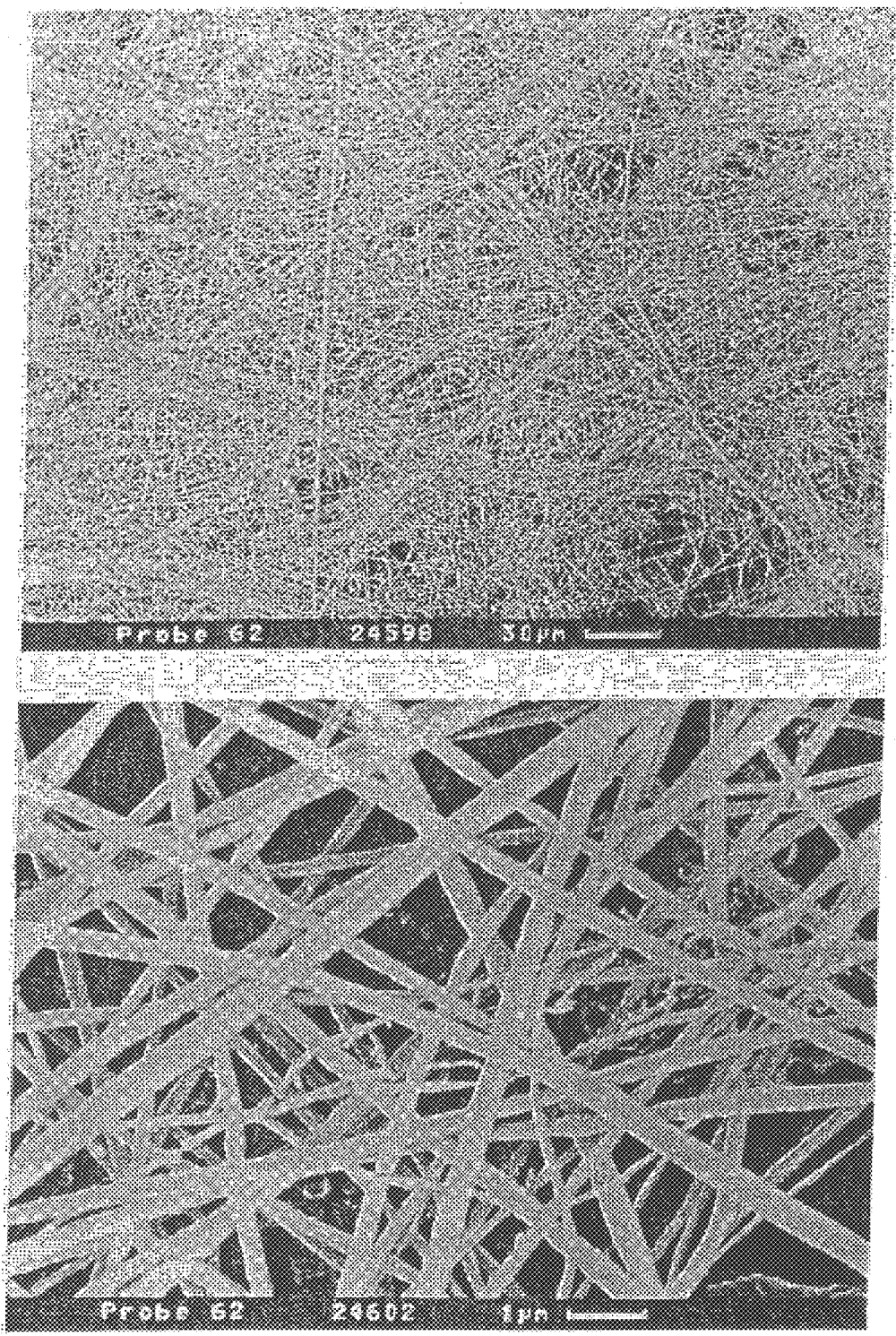

For use as a dielectric, the hollow fibers are preferably employed in the form of a nonwoven or mat (for example as shown in FIG. 2 or 3).

Due to the large surface area of the hollow fibers according to the invention, they can also be used in fuel cells, batteries or in electrochemical reactions. For such applications, the outer wall of the hollow fibers advantageously consists of oxygen ion conductors, such as, for example, perovskites. In oxidation reactions, starting material (for example an olefin) can flow around the hollow fibers, while oxygen is passed through the cavities of the fibers. The oxidation product is formed externally on the hollow fibers and transported away.

The hollow fibers according to the invention can be used as a catalytic system. Thus, for example, hollow fibers of noble metals, such as platinum or palladium, can be employed as denox catalysts in motor vehicles.

Hollow fibers according to the invention made from cell-compatible materials or having correspondingly modified surfaces can be incorporated or introduced into cell membranes and used for the separation and recovery or removal of metabolites, enzymes and other components of the cytoplasm within cells or cytoplasmitic components and thus for the recovery of bio-pharmaceuticals.

The following examples are intended to illustrate the invention in greater detail without restricting its scope.

EXAMPLE 1

Production of polylactide template fibers by electrostatic spinning without additives A 5% strength solution of poly-L-lactide in dichloromethane (conductivity<$10^{-7}$ $\mu$S/cm) was spun in the electrostatic spinning apparatus shown in FIG. 1 at a voltage of 35 kV. The separation of the cannula tip (diameter 0.3 mm) from the substrate plate (glass) was 10 cm. The fibers were used further without further treatment. A scanning electron photomicrograph of the fibers is shown in FIG. 2.

EXAMPLE 2

Production of polylactide template fibers by electrostatic spinning with additives A 5% strength solution of poly-L-lactide containing 1.5% of benzyltriethylammonium chloride (conductivity=417 $\mu$S/cm) was spun in the electrostatic spinning apparatus shown in FIG. 1 at a voltage of 35 kV. The separation of the cannula tip (diameter 0.3 mm) from the substrate plate (glass) was 10 cm. The fibers were used further without further treatment. A scanning electron photomicrograph of the fibers is shown in FIG. 3.

EXAMPLE 3

Figure 4:
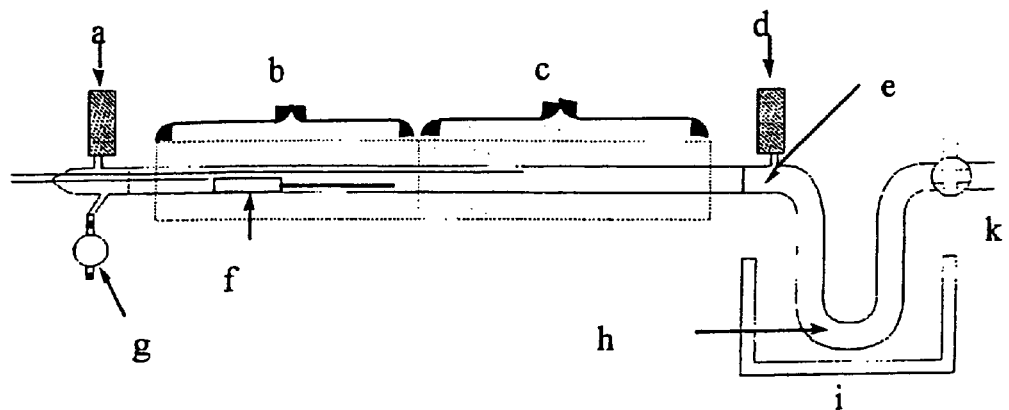
Figure 5:
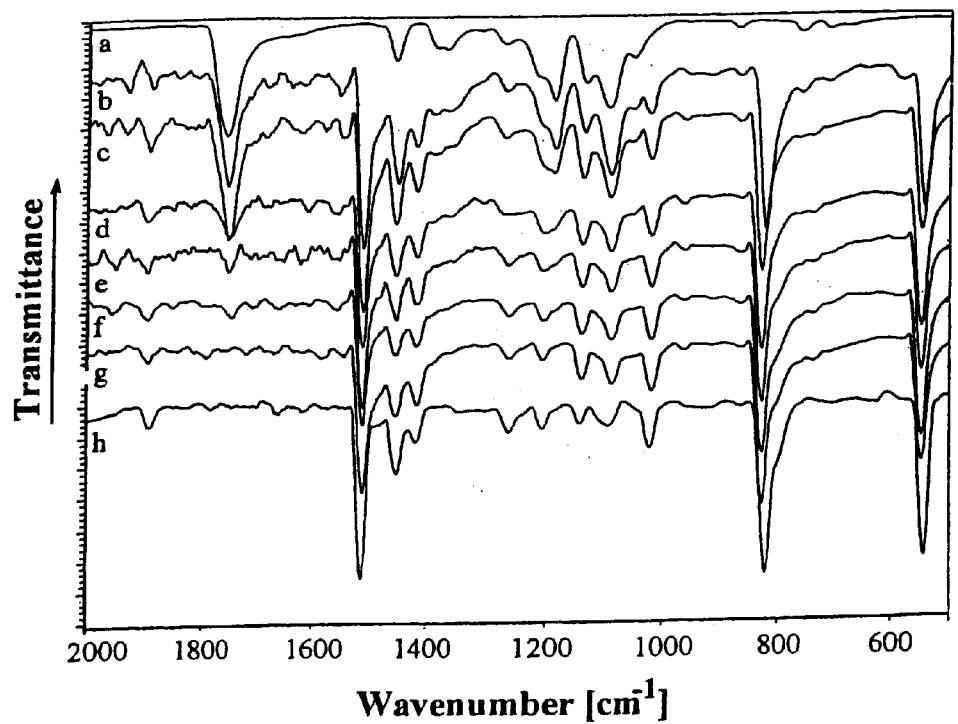
Figure 7:
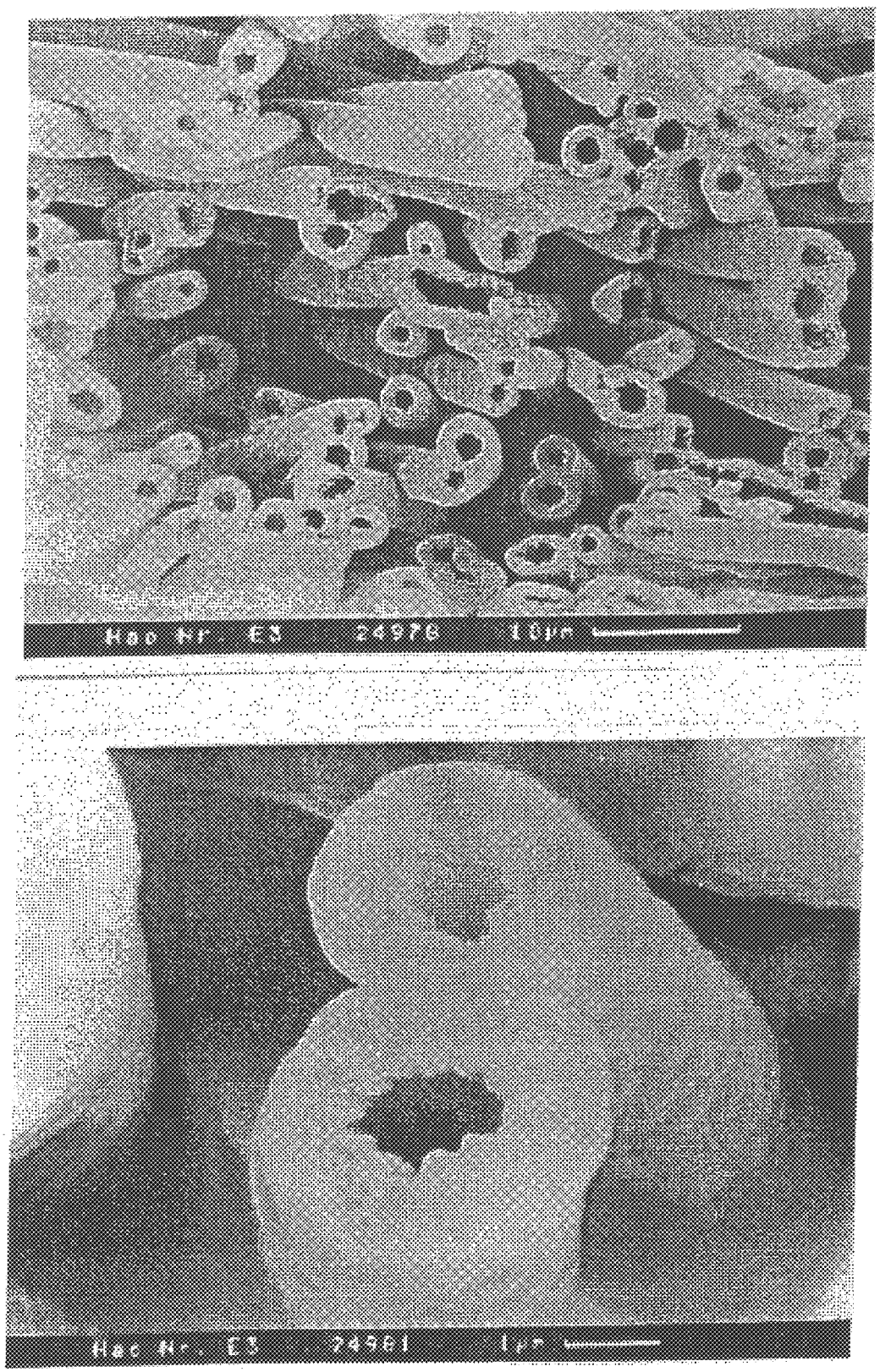
Figure 8:
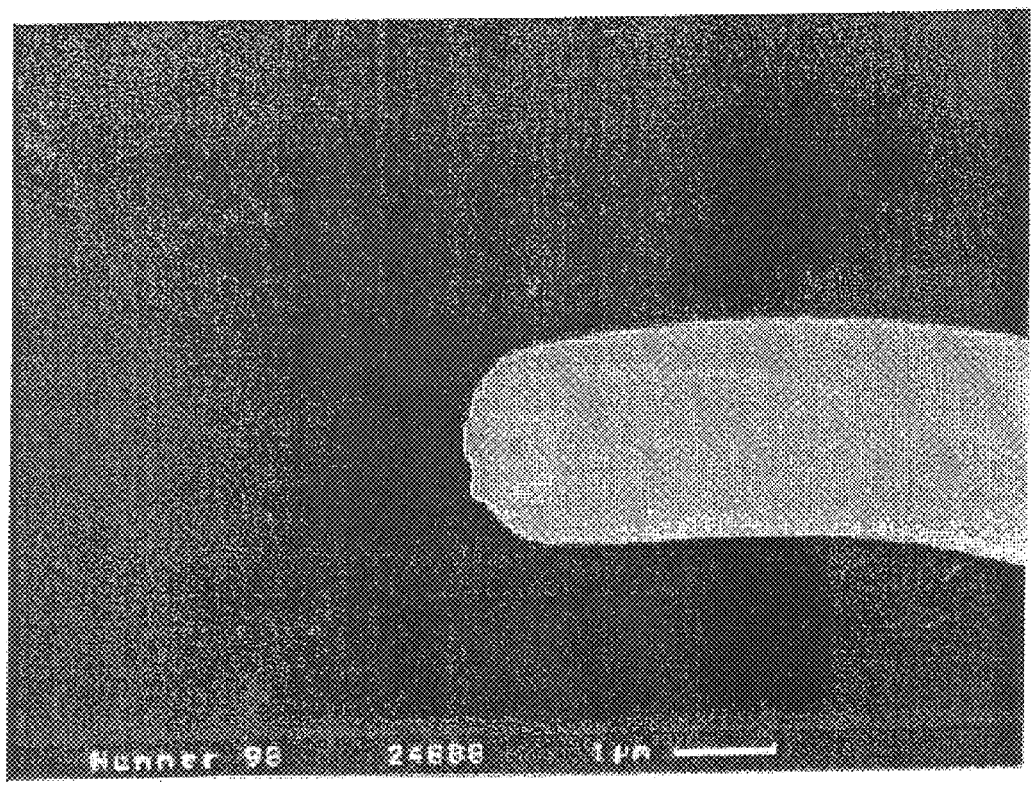

Production of poly(p-xylylene) hollow fibers by coating from the gas phase Polylactide template fibers produced by electrostatic spinning as described in Example 1 were placed in the sample chamber of the gas-phase deposition apparatus shown in FIG. 4. 230 mg of analytically pure [2.2] paracyclophane were evaporated at 220° C./0.1 mbar and pyrolyzed at 800° C., causing the formation of poly(p-xylylene) (PPX) in the sample chamber at about 20° C. The poly(p-xylylene)/polylactide composite fabric was thermally treated for 8 hours in a vacuum oven at 275° C./0.01 bar. The degradation of the polylactide template fibers was confirmed by infra-red spectroscopy (FIG. 5). The formation of poly(p-xylylene) hollow fibers having an internal diameter of about 2 µm–0.1 µm was confirmed by scanning electron microscopy (FIGS. 7 and 8).

Poly(p-xylylene) hollow fibers produced in this way have a density of 0.15 g/cm$^3$ and a DC of 1.29 (air=1). A nonwoven material made from such fibers consists of about 14% by vol. of poly(p-xylylene) and 86% by vol. of air.

EXAMPLE 4

Figure 10:
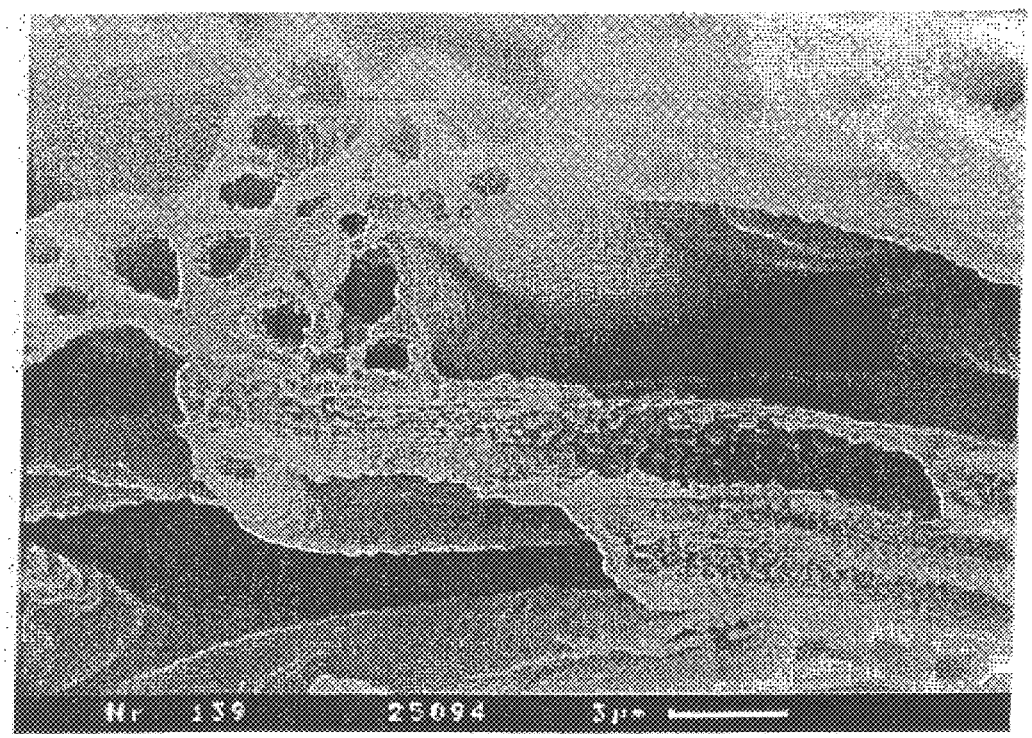

Production of polyimide hollow fibers by coating from solution Polylactide template fibers produced by electrostatic spinning as described in Example 1 were coated with 4% strength polyamidocaroxylic acid in water/DMF/pyridine by immersion. The polyamidocarboxylic acid/polylactide composite fabric was thermally treated for 9 hours in a vacuum oven at 150–285° C./0.01 mbar. During this treatment, firstly the polylactide template fibers were thermally degraded, and the polyamidocarboxylic acid was converted into polyimide. Formation of polyimide hollow fibers having internal diameters of about 1 µm–0.5 µm was confirmed by scanning electron microscopy (FIG. 10).

EXAMPLE 5

Figure 11:
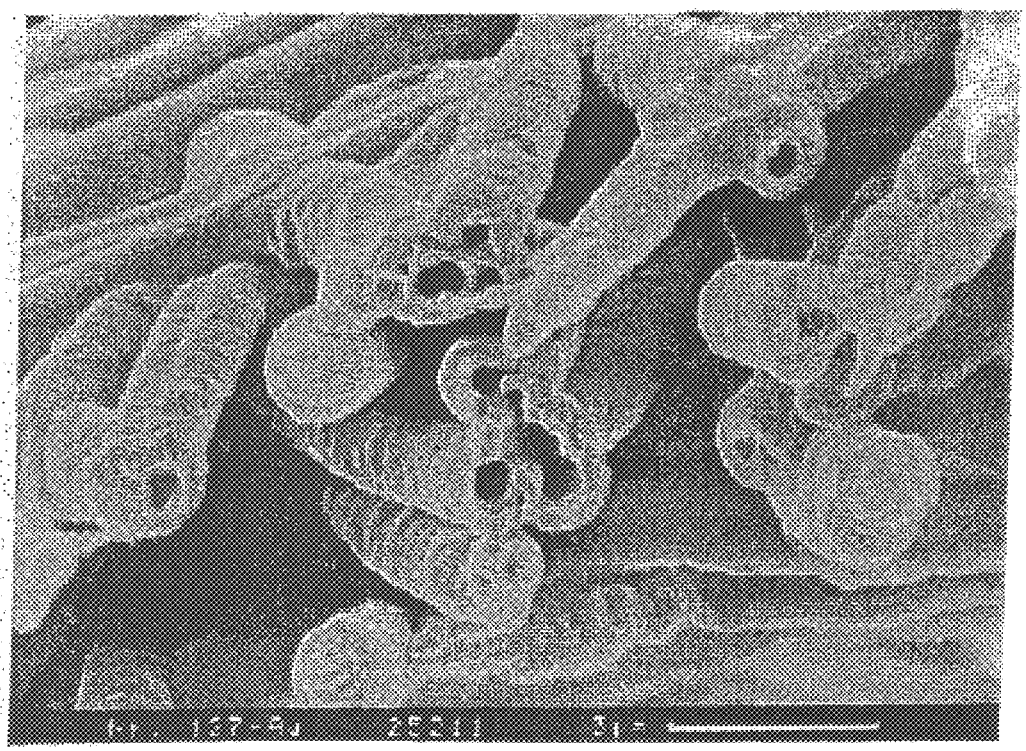

Production of poly(p-xylylene)/gold hollow fibers by coating from the gas phase Polylactide template fibers produced by electrostatic spinning (with 0.8% of benzyltriethylammonium chloride as additive in dichloromethane) as described in Example 2 were coated with gold from the gas phase in a vapor-deposition apparatus. These polylactide/gold fibers were subsequently placed in the sample chamber of the gas-phase deposition apparatus shown in FIG. 4. 200 mg of analytically pure [2.2]paracyclophane were subsequently evaporated at 220° C./0.1 mbar and pyrolyzed at 700° C., causing the formation of poly(p-xylylene) in the sample chamber at about 20° C. The poly(p-xylylene)/polylactide composite fabric was thermally treated for 8 hours in a vacuum oven at 285° C./0.01 mbar. The formation of poly(p-xylylene)/gold hollow fibers having a mean internal diameter of about 0.3 µm was confirmed by scanning electron microscopy (FIG. 11). The presence of the gold coating on the internal wall of the poly(p-xylylene) hollow fibers was confirmed by element-specific scanning electron microscopy.

EXAMPLE 6

Figure 12:
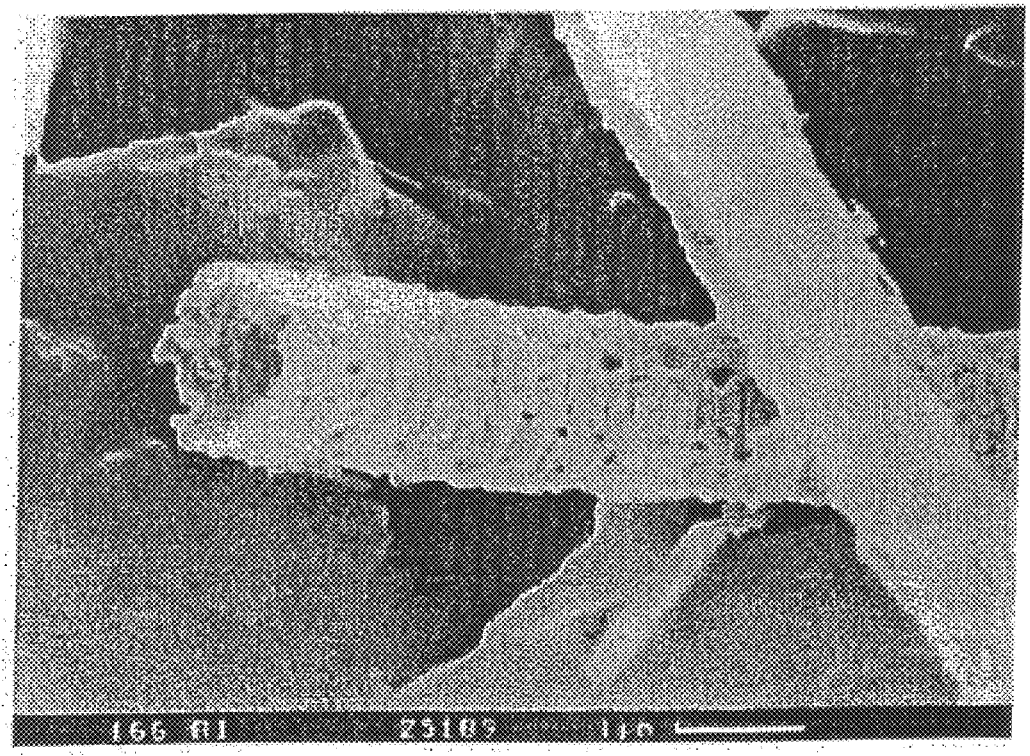

Production of aluminum hollow fibers by coating from the gas phase Polylactide template fibers produced by electrostatic spinning (with 0.8% of benzyltriethylammonium chloride as additive in dichloromethane) as described in Example 2 were coated with aluminum from the gas phase in a vapor-deposition apparatus. These polylactide/aluminum fibers were subsequently thermally treated for 8 hours in a vacuum oven at 285° C./0.01 mbar. The formation of aluminum hollow fibers having a mean internal diameter of about 0.5 µm was confirmed by scanning electron microscopy (FIG. 12). The presence of aluminum was detected by element-specific scanning electron microscopy.

EXAMPLE 7

Figure 13:
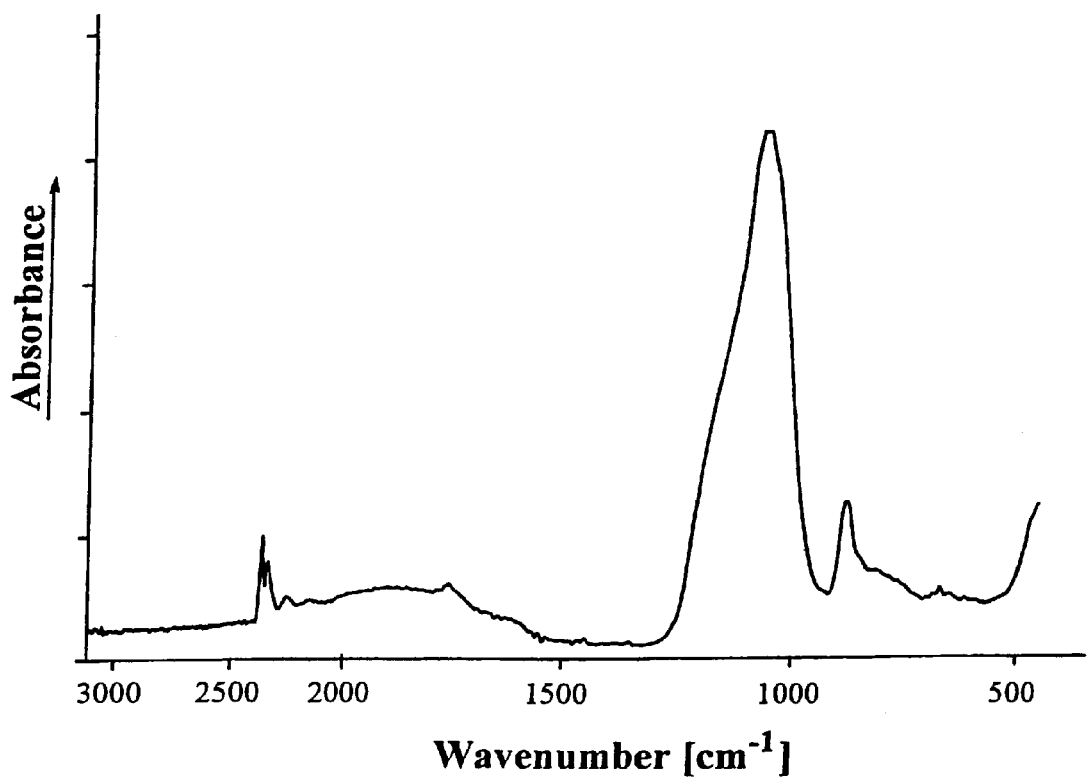
Figure 14:
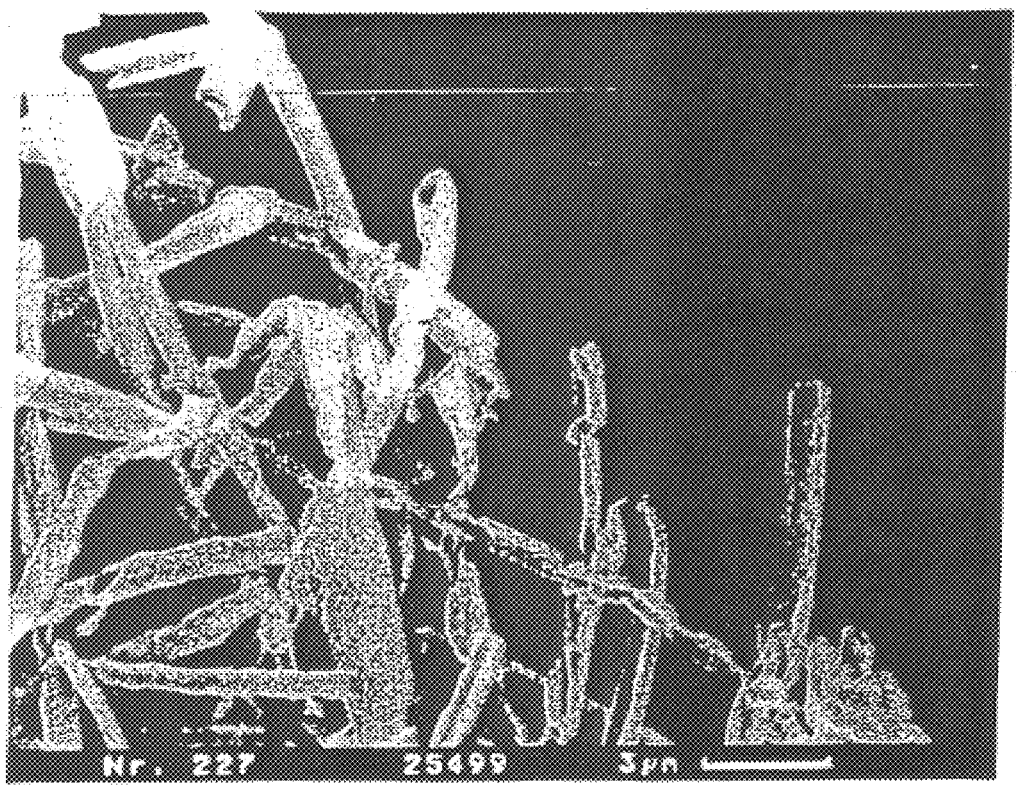

Production of glass hollow fibers by coating from the gas phase Polylactide template fibers produced by electrostatic spinning as described in Example 2 (with 0.8% of benzyl-triethylammonium chloride as additive in dichloromethane) were coated with silicon monoxide from the gas phase in a vapor-deposition apparatus and converted into silicon dioxide by means of oxygen (glass, detected by infra-red and wide-angle X-ray spectroscopy (WAXS)). These polylactide/glass fibers were subsequently thermally treated for 14 hours in a vacuum oven at 285° C./0.01 bar. It was found by means of IR spectroscopy that the thermal degradation of the polylactide template fibers is quantitative (FIG. 13). The formation of glass hollow fibers having a mean internal diameter of about 0.5 µm was confirmed by scanning electron microscopy (FIG. 14).

KEY TO THE FIGURES

FIG. 1. Diagrammatic representation of an electrostatic spinning apparatus

FIG. 2. Polylactide template fibers produced by electrostatic spinning from dichloromethane without additive (Example 1)

FIG. 3. Polylactide template fibers produced by electrostatic spinning from dichloromethane with additive (Example 2)

FIG. 4. Diagrammatic representation of a gas-phase deposition apparatus for poly(p-xylylene), with a) pressure measurement, b) evaporation zone, c) pyrolysis zone, d) pressure measurement, e) sample chamber, f) quartz boat for starting material, g) recipient for pressure regulation, h) pyrolysis oils, i) cold trap, k) vacuum FIG. 5. Infra-red spectroscopy investigation of the thermal degradation of poly(p-xylylene)-coated polylactide template fibers at 265° C./0.01 bar and various times b=0 hours, c=1 hour, d=2 hours, e=3 hours, f=4 hours, g=6 hours, and the pure polymer polylactide=a and poly(p-xylylene)=h.

Figure 6:
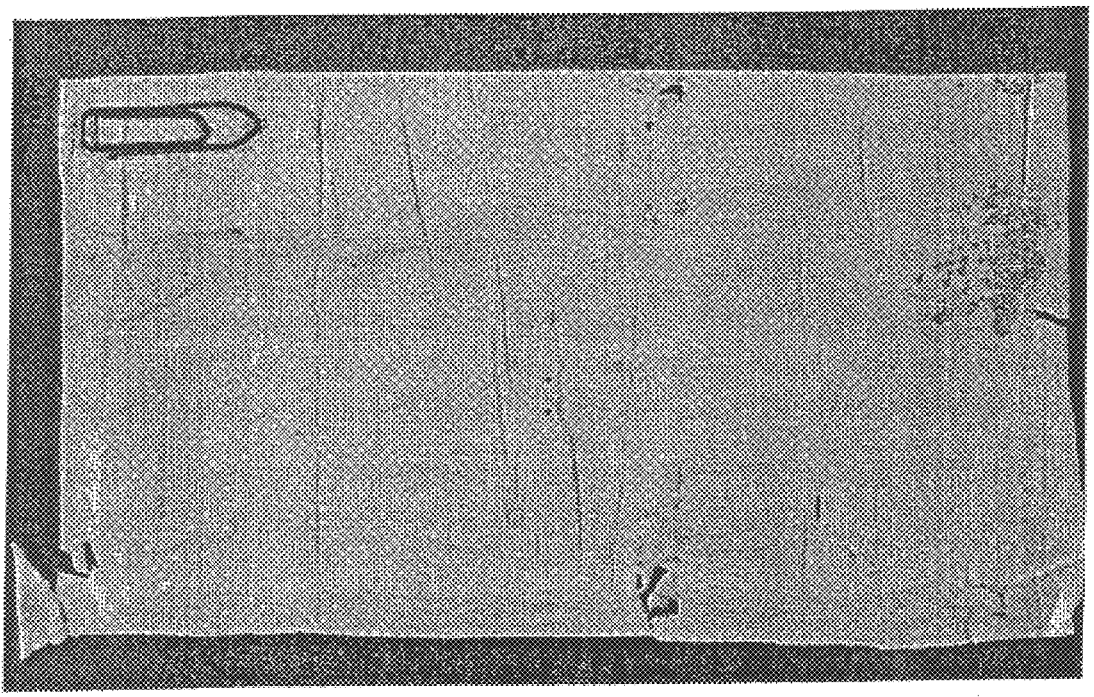

FIG. 6. Photograph of a poly(p-xylylene) hollow fiber fabric

FIG. 7. Scanning electron photomicrographs of poly(p-xylylene) hollow fibers after removal of the polylactide template fibers (Example 3).

FIG. 8. Scanning electron photomicrographs of poly(p-xylylene) hollow fibers after removal of the polylactide template fibers (the polylactide template fibers produced by electrostatic spinning from dichloromethane with 0.8% of benzyltriethylammonium trichloride)

Figure 9:
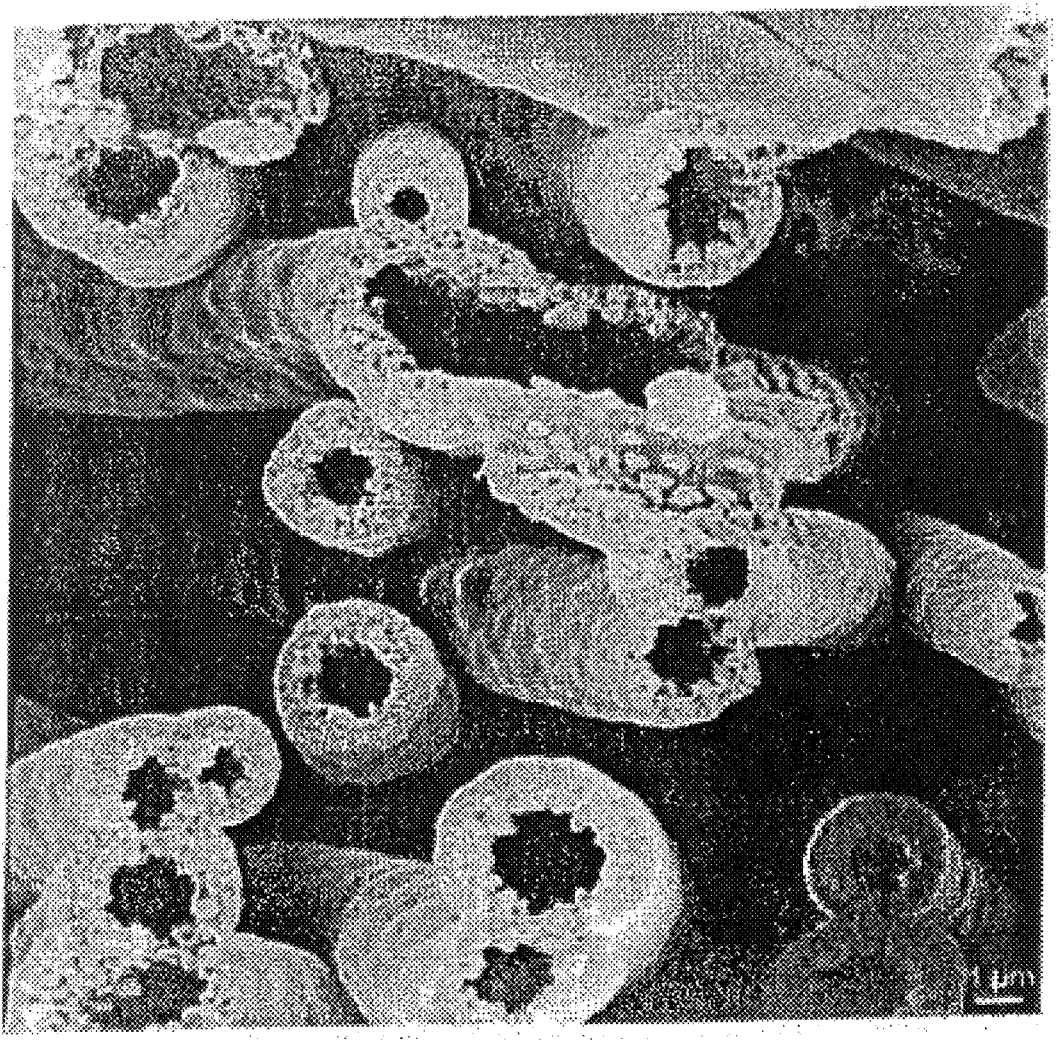

FIG. 9. Scanning electron photomicrograph of poly(p-xylylene) hollow fibers after removal of the polylactide template fibers with a view of the topology of the hollow fiber interior walls.

FIG. 10. Scanning electron photomicrograph of polyimide hollow fibers after removal of the polylactide template fibers (Example 4).

FIG. 11. Scanning electron photomicrograph of PPX hollow fibers after removal of the polylactide template fibers with an internal gold coating (Example 5)

FIG. 12. Scanning electron photomicrograph of aluminum hollow fibers after removal of the polylactide template fibers (Example 6)

FIG. 13. Infra-red spectrum of the glass hollow fibers after degradation of the polylactide template fibers FIG. 14. Scanning electron photomicrograph of glass hollow fibers

What is claimed is:

1. A fiber comprising a hollow fiber having an internal diameter of from 10 nm to 1 µm filled with a core material, its wall comprising one or more inorganic metal-containing compounds, polymers, metals or combinations thereof, wherein the core material has a mean separation from the inner wall of the hollow fiber of from 10 to 3000 nm.

2. The fiber as claimed in claim 1, wherein its wall comprises poly(p-xylylene), polyacrylamide, polyimides, polyesters, polyolefins, polycarbonates, polyamides, polyethers, polyphenylene, polysilanes, polysiloxanes, polybenzimidazoles, polybenzothiazoles, polyoxazoles, polysulfides, polyester amides, polyarylenevinylenes, polylactides, polyether ketones, polyurethanes, polysulfones, ormocers, polyacrylates, silicones, fully aromatic copolyesters, poly-N-vinylpyrrolidone, polyhydroxyethyl methacrylate, polymethyl methacrylate, polyethylene terephthalate, polybutylene terephthalate, polymethacrylonitrile, polyacrylonitrile, polyvinyl acetate, neoprene, Buna N, polybutadiene, polytetrafluoroethene, modified cellulose, unmodified cellulose, alginates, collagen, homopolymers, copolymers or blends thereof.

3. The fiber as claimed in claim 1, wherein its wall comprises a plurality of metals from groups Ia, Ib, IIa, IIb, IIIa, IIIb, IVa, IVb, Vb, VIb, VIIb or VIII of the Periodic Table, wherein said metals are present as pure metals or an alloy.

4. The fiber as claimed in claim 1, wherein its wall comprises a plurality of layers.

5. The fiber as claimed in claim 1, wherein the core material comprises a plurality of inorganic compounds, ceramic fibers, carbon fibers, polymers, metals or combinations thereof.

6. The fiber as claimed in claim 1, wherein said fiber has a dielectric constant of less than 4.

7. A process for the production of a fiber according to claim 1, which comprises coating a fiber of a first non-degradable material successively with a second degradable material and at least one further material and degrading the second degradable material.

8. The process as claimed in claim 7, wherein the further material comprises polymers, metals or combinations thereof.

9. The process as claimed in claim 7, wherein the further material comprises poly(p-xylylene), polyacrylamide, polyimides, polyesters, polyolefins, polycarbonates, polyamides, polyethers, polyphenylene, polysilanes, polysiloxanes, polybenzimidazoles, polybenzothiazoles, polyoxazoles, polysulfides, polyester amides, polyarylenevinylenes, polylactides, polyether ketones, polyurethanes, polysulfones, ormocers, polyacrylates, silicones, fully aromatic copolyesters, poly-N-vinylpyrrolidone, polyhydroxyethyl methacrylate, polymethyl methacrylate, polyethylene terephthalate, polybutylene terephthalate, polymethacrylonitrile, polyacrylonitrile, polyvinyl acetate, neoprene, Buna N, polybutadiene, polytetrafluoroethene, modified cellulose, unmodified cellulose, alginates, collagen, homopolymers, copolymers or blends thereof.

10. The process as claimed in claim 7, wherein the further material comprises a plurality of metals from groups Ia, Ib, IIa, IIb, IIIa, IIIb, IVa, IVb, Vb, VIb, VIIb or VIII of the Periodic Table, wherein said metals are present as pure metals or an alloy.

11. The process as claimed in claim 7, wherein the further material is obtained by polymerization of one or more monomers.

12. The process as claimed in claim 11, wherein the further material is obtained by homo- or copolymerization of methacrylate, styrene, styrene sulfonate, 1,6-hexamethylene diisocyanate (HDI), 4,4'-methylenebiscyclohexyl diisocyanate (HMDI), 4,4'-methylenebis(benzyl diisocyanate) (MDI), 1,4-butanediol, ethylenediamine, ethylene, styrene, butadiene, 1-butene, 2-butene, vinyl alcohol, acrylonitrile, methyl methacrylate, vinyl chloride, fluorinated ethylenes, terephthalate or combinations thereof.

13. The process as claimed in claim 7, wherein the degradation of the degradable material is carried out thermally, chemically, biologically, radiation-induced, photochemically, by means of plasma, ultrasound or extraction with a solvent.

14. A separation or storage medium for gases, liquids or particle suspensions comprising the fiber claimed in claim 1.

15. An ion exchanger for dialysis, an artificial lung, a protein store, a controlled release or drug delivery system, or a filter in a medical separation method comprising the fiber claimed in claim 1.

16. A separation method comprising contacting a solution or suspension, said solution or suspension comprising a plurality of metabolites, enzymes or other components of a cytoplasm, with the fiber claimed in claim 1.

17. A sensor constituent, a microreactor, a wire, a cable or a capacitor comprising the fiber claimed in claim 1.

18. A composite material, a filler, a mechanical reinforcement or a heat insulator comprising the fiber claimed in claim 1.

19. A fuel cell, battery or electrochemical reaction comprising the fiber claimed in claim 1.

20. A capillary electrophoresis instrument, a scanning probe microscope, or a catalytic system comprising the fiber claimed in claim 1.

21. A dielectric material comprising the fiber claimed in claim 1.

22. An interlayer dielectric for chip manufacture comprising the fiber as claimed in claim 1.

23. A hollow fiber having an internal diameter of from 10 nm to 1 $\mu$m and an outer wall comprising one or more inorganic metal-containing compounds, polymers, metals or combinations thereof, said hollow fiber being prepared by coating, at least once, a degradable template fiber made by electrostatic spinning with one or more polymers, and subsequently degrading the degradable template fiber.

24. The hollow fiber as claimed in claim 23, wherein the outer wall of the hollow fiber comprises poly(p-xylylene), polyacrylamide, polyimides, polyesters, polyolefins, polycarbonates, polyamides, polyethers, polyphenylene, polysilanes, polysiloxanes, polybenzimidazoles, polybenzothiazoles, polyoxazoles, polysulfides, polyester amides, polyarylenevinylenes, polylactides, polyether ketones, polyurethanes, polysulfones, ormocers, polyacrylates, silicones, fully aromatic copolyesters, poly-N-vinylpyrrolidone, polyhydroxyethyl methacrylate, polymethyl methacrylate, polyethylene terephthalate, polybutylene terephthalate, polymethacrylonitrile, polyacrylonitrile, polyvinyl acetate, neoprene, Buna N, polybutadiene, polytetrafluoroethene, modified cellulose, unmodified cellulose, alginates, collagen, homopolymers, copolymers or blends thereof.

25. The hollow fiber as claimed in claim 23, wherein the outer wall of the hollow fiber comprises a plurality of metals from groups Ia, Ib, IIa, IIb, IIIa, IIIb, IVa, IVb, Vb, VIb, VIIb or VIII of the Periodic Table, wherein said metals are present as pure metals or an alloy.

26. The hollow fiber as claimed in claim 23, wherein the outer wall of the hollow fiber comprises a plurality of layers.

27. A fiber comprising the hollow fiber as claimed in claim 23, filled with a core material.

28. The fiber as claimed in claim 27, wherein the core has a mean separation from the inner wall of the hollow fiber of from 10 to 300 nm.

29. The hollow fiber as claimed in claim 27, wherein the core comprises a plurality of inorganic compounds, ceramic fibers, carbon fibers, polymers, metals or combinations thereof.

30. The hollow fiber as claimed in claim 23, wherein said fiber has a dielectric constant of less than 4.

31. A process for the production of a hollow fiber according to claim 23, which comprises coating, at least once, a fiber of a first degradable template made by electrostatic spinning material with one or more polymers, metals or combinations thereof, and subsequently degrading the first material.

32. A process for the production of a hollow fiber according to claim 23, which comprises coating a fiber of a first non-degradable material successively with a second degradable material made by electrostatic spinning and at least one further material and degrading the second degradable material, wherein said hollow fiber has an internal diameter of from 10 nm to 1 µm, an outer wall of one or more polymers or metals and a core of said first material.

33. The process as claimed in claim 31, wherein the further material comprises polymers, metals or combinations thereof.

34. The process as claimed in claim 31, wherein the further material comprises poly(p-xylylene), polyacrylamide, polyimides, polyesters, polyolefins, polycarbonates, polyamides, polyethers, polyphenylene, polysilanes, polysiloxanes, polybenzimidazoles, polybenzothiazoles, polyoxazoles, polysulfides, polyester amides, polyarylenevinylenes, polylactides, polyether ketones, polyurethanes, polysulfones, ormocers, polyacrylates, silicones, fully aromatic copolyesters, poly-N-vinylpyrrolidone, polyhydroxyethyl methacrylate, polymethyl methacrylate, polyethylene terephthalate, polybutylene terephthalate, polymethacrylonitrile, polyacrylonitrile, polyvinyl acetate, neoprene, Buna N, polybutadiene, polytetrafluoroethene, modified cellulose, unmodified cellulose, alginates, collagen, homopolymers, copolymers or blends thereof.

35. The process as claimed in claim 31, wherein the further material comprises a plurality of metals from groups Ia, Ib, IIa, IIb, IIIa, IIIb, IVa, IVb, Vb, VIb, VIIb or VIII of the Periodic Table, wherein said metals are present as pure metals or an alloy.

36. The process as claimed in claim 31, wherein the further material is obtained by polymerization of one or more monomers.

37. The process as claimed in claim 36, wherein the further material is obtained by homo- or copolymerization of methacrylate, styrene, styrene sulfonate, 1,6-hexamethylene diisocyanate (HDI), 4,4'-methylenebiscyclohexyl diisocyanate (HMDI), 4,4'-methylenebis(benzyl diisocyanate) (MDI), 1,4-butanediol, ethylenediamine, ethylene, styrene, butadiene, 1-butene, 2-butene, vinyl alcohol, acrylonitrile, methyl methacrylate, vinyl chloride, fluorinated ethylenes, terephthalate or combinations thereof.

38. The process as claimed in claim 31, wherein the degradation of the degradable material is carried out thermally, chemically, biologically, radiation-induced, photochemically, by means of plasma, ultrasound or extraction with a solvent.

39. A separation or storage medium for gases, liquids or particle suspensions comprising the hollow fiber claimed in claim 23.

40. An ion exchanger for dialysis, an artificial lung, a protein store, a controlled release or drug delivery system, or a filter in a medical separation method comprising the hollow fiber claimed in claim 23.

41. A separation method comprising contacting a solution or suspension, said solution or suspension comprising a plurality of metabolites, enzymes or other components of a cytoplasm, with the hollow fiber claimed in claim 23.

42. A sensor constituent, a microreactor, a wire, a cable or a capacitor comprising the hollow fiber claimed in claim 23.

43. A composite material, a filler, a mechanical reinforcement or a heat insulator comprising the hollow fiber claimed in claim 23.

44. A fuel cell, battery or electrochemical reaction comprising the hollow fiber claimed in claim 23.

45. A capillary electrophoresis instrument, a scanning probe microscope, or a catalytic system comprising the hollow fiber claimed in claim 23.

46. A dielectric material comprising the hollow fiber claimed in claim 23.

47. An interlayer dielectric for chip manufacture comprising the hollow fiber as claimed in claim 23.

* * * * *

UNITED STATES PATENT AND TRADEMARK OFFICE
CERTIFICATE OF CORRECTION

PATENT NO. : 6,667,099 B1
DATED : December 23, 2003
INVENTOR(S) : Greiner et al.

It is certified that error appears in the above-identified patent and that said Letters Patent is hereby corrected as shown below:

<u>Title page,</u>
Item [30], should read:
-- [30]  Foreign Application Priority Data
Jul. 29, 1999    (DE) ………….. 199 35 388
May 12, 2000   (DE) ………….. 100 23 456 --

<u>Title page, Item [54] and Column 1,</u>
Title, should read:
-- [54]  MESO- AND NANOTUBES --

Signed and Sealed this

Fourth Day of May, 2004

JON W. DUDAS
*Acting Director of the United States Patent and Trademark Office*